United States Patent [19]

Woods et al.

[11] Patent Number: 5,113,003
[45] Date of Patent: May 12, 1992

[54] SILICON-CONTAINING PHENOXY ETHERS, POLYMERS THEREOF, AND USE OF SUCH POLYMERS

[75] Inventors: John G. Woods, Farmington, Conn.; Pauline Coakley, County Kilkenny, Ireland

[73] Assignee: Loctite (Ireland) Limited, Dublin, Ireland

[21] Appl. No.: 672,221

[22] Filed: Mar. 20, 1991

[30] Foreign Application Priority Data

Mar. 20, 1990 [IE]  Ireland ................................ 1013/90

[51] Int. Cl.⁵ .............................................. C07F 7/18
[52] U.S. Cl. ................................... 556/432; 556/436; 556/443; 556/453; 556/457; 556/465; 556/482; 568/420; 568/111; 568/425; 568/630; 568/671; 568/715; 568/840; 568/908; 549/369; 549/430
[58] Field of Search ............... 556/432, 436, 443, 486, 556/453, 457, 465, 482; 568/420, 425, 630, 671, 715, 840, 908; 549/369, 430

[56] References Cited

U.S. PATENT DOCUMENTS

| | | | |
|---|---|---|---|
| 3,936,557 | 2/1976 | Watt et al. ........................... | 525/482 |
| 4,116,886 | 9/1978 | Cella et al. .......................... | 528/88 |
| 4,173,551 | 11/1979 | Crivello et al. ..................... | 523/457 |
| 4,431,774 | 2/1984 | Felder-Schraner et al. ........ | 525/162 |
| 4,504,372 | 3/1985 | Kirchmayr et al. ................. | 525/42 |
| 4,510,290 | 4/1985 | Kirchmayr et al. ................. | 525/162 |
| 4,537,923 | 8/1985 | Slongo et al. ....................... | 564/100 |
| 4,540,598 | 9/1985 | Berner et al. ....................... | 427/54 |
| 4,640,937 | 2/1987 | Hanyuda et al. .................... | 522/31 |

FOREIGN PATENT DOCUMENTS

| | | |
|---|---|---|
| 0309291 | 3/1989 | European Pat. Off. |
| 0311371 | 4/1989 | European Pat. Off. |

OTHER PUBLICATIONS

Li Bassi, J. Rad. Curing, Jul. 1987, 18-31.

*Primary Examiner*—Jose G. Dees
*Assistant Examiner*—Joseph M. Conrad

*Attorney, Agent, or Firm*—Edward K. Welch, II; Eugene F. Miller

[57] ABSTRACT

The silicon-containing phenoxy ethers are of the formula III:

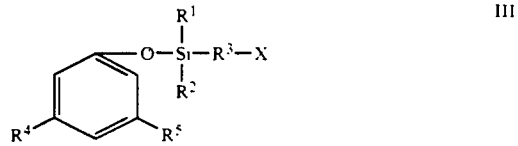

wherein
$R^1$ and $R^2$ which may be the same or different are selected from H, $-R^3-X$, aliphatic hydrocarbyl having 1-6 carbon atoms or aryl, or substituted derivatives thereof, provided that not more than one of $R^1$ and $R^2$ is H;
$R^3$ is a divalent $C_1-C_{30}$ aliphatic and/or aromatic hydrocarbyl group which may optionally be substituted, or interrupted, by a hetero atom;
$R^4$ and $R^5$ which may be the same or different are H,

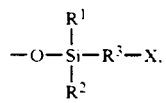

or an ortho para directing activating group for aromatic electrophilic substitution, other than an amine;

and X is a reactive functional group capable of undergoing an acid-catalyzed electrophilic aromatic substitution reaction with a phenol, for example an aldehyde group. They can be polymerized to produce silicone-modified polymers of the phenol-aldehyde type without the use of free aldehyde. One-part compositions containing a compound of the formula III and a latent acid catalyst (e.g. for photoinitiation or thermal initiation of polymerization) are described. The compositions are intended for use as coatings, sealants, adhesives, potting compositions or photoresists.

Exemplified compounds are of the formula VII:

VII

-continued or X

X

6 Claims, 2 Drawing Sheets

SILICON-CONTAINING PHENOXY ETHERS, POLYMERS THEREOF, AND USE OF SUCH POLYMERS

BACKGROUND OF THE INVENTION a) Field of the Invention

This invention relates to silicon-containing phenoxy ethers, polymers thereof, and use of such polymers, particularly in compositions for use as coatings, sealants, adhesives, potting compositions or photoresists.

b) Description of the Related Art

U.S. Pat. No. 4,640,937 Hanyuda describes a modified phenolic resinous composition curable with active energy rays comprising a phenolic compound, an unsaturated cycloacetal, and an onium salt. However compositions based on such modified phenolic compounds are of limited interest.

European Pat. Publication No. 0,311,371 (application No. 88309271.0) describes a cationically curable composition comprising:

a compound A which may be a phenoxy silyl ether of the formula I wherein $R_c$ and $R_d$ are H, hydrocarbyl having 1-5 carbon atoms, or aryl;
$R_e$ is H, hydrocarbyl, aryl, hydrocarbylarly or a halogen-substituted derivative thereof;
$R_a$ and $R_b$ (which may be the same or different) are H or an ortho para directing activating group for aromatic electrophilic substitution, other than an amine; provided that $R_a$ and $R_b$ are not both H;

a compound B selected from formaldehyde, monofunctional aldehydes other than formaldehyde, and multi-functional aldehydes; and compounds capable of producing such aldehydes in the presence of acid;

and a compound C which is a latent acid catalyst.

Example 11 of European Pat. Publication No. 0,309,291 describes the preparation of a formulation of bis-1,3-(trimethylsiloxy)-benzene of the formula II:

together with paraldehyde and a photoinitiator. However bis-1,3-(trimethylsiloxy)-benzene is not very stable in the presence of acid and upon removal of the trimethylsily groups there is a risk of producing unreactive siloxane components, particularly a siloxane dimer which interferes with adhesive properties.

SUMMARY OF THE INVENTION

The present invention provides compounds of the formula III:

wherein
$R^1$ and $R^2$ which may be the same or different are H, $-R^3-X$, aliphatic hydrocarbyl having 1-6 carbon atoms or aryl, or substituted derivtaives thereof, provided that not more than one of $R^1$ or $R^2$ is H;
$R^3$ is a divalent $C_1-C_{30}$ aliphatic and/or aromatic hydrocarbyl group which may optionally be substituted, or interrupted by, a hetero atom;
$R^4$ and $R^5$ which may be the same or different are or an ortho para directing activating group for aromatic electrophilic substitution, other than an amine;

and X is a reactive functional group capable of undergoing an acid-catalysed electrophilic aromatic substitution reaction with a phenol.

Preferably X is selected from:

(a) aldehyde groups (b) cyclic unsaturated acetal groups of the structure or where $R_7 =$ H or $CH_3$

(c) benzylic alcohol groups having the structure IV (i), (ii) or (iii):

or

-continued which may be further ring substituted with —CH$_3$ groups.

(d) tertiary aliphatic alcohol groups of the structure (e) allylic ether groups of the structure

R-—CH=CH—CH$_2$—O—

(f) propenylbenzene derivatives of the structure V (g) allylic alcohol groups of the structure

HO—CH$_2$—CH=CH—

(h) alkenes of the structure where R- is as defined above.

Most preferably X is as defined at (a), (b), or (c), particularly (a), above.

Preferably R$^4$ and R$^5$ which may be the same or different are selected from $C_1$-$C_{20}$ alkyl (more particularly $C_1$-$C_4$ alkyl), $C_1$-$C_{20}$ alkenyl, $C_1$-$C_{20}$ alkoxy, phenoxy, and —NHC(O)R$^6$ (wherein R$^6$=$C_1$-$C_{16}$ alkyl or phenyl).

More preferably R$^4$ and R$^5$ are selected from

—CH$_3$, —OCH$_3$, —(CH$_2$)$_7$ CH=CH—(CH$_2$)$_5$ CH$_3$, —(CH$_2$)$_7$ CH=CH—CH$_2$—CH=CH—(CH$_2$)$_2$ CH$_3$ and —(CH$_2$)$_7$ CH=CH—CH$_2$—CH=CH—CH$_2$—CH=CH$_2$ wherein the 3 last-mentioned structures indicate C$_{15}$ side chains of the kind found as meta-substituents on mono- and diphenols present in cashew nut shell liquid (see "Phenolic Resins" by A. Knop and L.A. Pilato, Springer-Verlag, 1985, page 13).

Most preferably R$^5$ is H and R$^4$ is

The most preferred group of compounds in accordance with the present invention is of the formula VI wherein R$^1$ and R$^2$ are as defined above,
Ph is phenyl,
m=0 or 1, and
n=1-10, preferably 1-6 when m=1.

Preferably R$^1$ and R$^2$ are $C_1$-$C_4$ alkyl, more particularly —CH$_3$.

The term "aliphatic hydrocarbyl" as used herein includes alkyl, alkenyl and alkynyl. Aliphatic hydrocarbyl groups shall preferably contain from 1 to 10 carbon atoms, and aryl and hydrocarbylarly groups shall preferably have from 6 to 20 carbon atoms, more preferably from 6 to 10 carbon atoms. A substituted derivative of the foregoing may suitably be substituted with one or more halo groups or substituted or interrupted by one or more oxo groups for example an ether group, a ketone group or an ester group. Halogen may be chlorine, bromine, fluorine or iodine.

The compounds of the present invention are capable of acid-catalysed hydrolysis and condensation polymerisation to form phenolic resins which can be further crosslinked.

The invention therefore also provides polymers of the compounds of formula III as defined above, either in the form of cross-linkable resins or as crosslinked polymers. The invention further provides compositions based on the said compounds or polymers together with a latent acid catalyst.

Curing may be effected by photoinitiation, by thermal initiation or by moisture triggered curing using a latent initiator of the kind described in U.S. Pat. No. 4,116,886 Cella. The compositions therefore preferably are one-part compositions containing a small quantity (e.g. 0.1-10%, preferably 1-5%, by weight of the composition) of a dissolved or dispersed photochemical, moisture-sensitive or thermally labile acid catalyst.

The latent acid catalyst is preferably material which generates acid on exposure to radiation, particularly a material which is activated by ultraviolet or visible radiation in the wavelength range 200 to 800 nm. Such materials include diazonium salts (*); iodonium and idosyl salts (*); sulphonium and sulphoxonium salts (*); pi-arene metal complexes (*); tris-beta-diketone aluminium complexes with triarylsilylperoxides or o-nitrobenzyl(triarylsilyl)- ethers (*); *See Li Bassi, Photoinitiators of Polymerisation: Recent Developments and Evolution, J. Rad. Curing. Jul. 1987, 18-31); alpha-sulphonyloxy esters (U.S. Pat. No. 4,510,290); beta-sulphonyloxy esters (U.S. Pat. No. 4,504,372); oxime sulphonates (U.S. Pat. No. 4,540,598); quinolinium sulphonates (U.S. Pat. No. 4,431,774) and pyrylium salts (Irish Pat. application No. 2158/85).

However, materials which generate acid on exposure to heat or to moisture are also suitable. Such materials include for example the dicarbonyl chelates of main row elements of groups IIIA-VA described in U.S. Pat. No. 4,116,886 Cella, which are moisture sensitive; diazonium salts described in U.S. Pat. No. 3,936,557 Watt, which are activatable by heat or radiation; polyalkylpiperidinesulphonic acid esters described in U.S. Pat. No. 4,537,923 Slongo et al; and iodonium salts described in U.S. Pat. No. 4,173,551 Crivello, which are activatable by heat.

The compounds may also be cured by the direct addition of acids or acid-producing redox catalysts or may be cured by contacting the composition with a surface of sufficient acidity e.g. to which an acidic activator has been applied.

The compositions may also contain other ingredients or additives which are compatible therewith and which in particular do not induce spontaneous polymerization nor inhibit the acid-initiated phenol-aldehyde condensation reaction. Such other ingredients or additives include inorganic fillers, pigments and dyestuffs, plasticizers, toughening agents, adhesion promoters, flow control additives, fire retardants, and stabilizers.

The present invention produces non-brittle silicone-modified polymers of the phenol-alkehyde type without the use of free aldehyde. The compositions are easier to formulate and safer to handle than conventional phenol-/aldehyde or phenolic-resin based compositions, particularly compositions prepared from resorcinol which is toxic and difficult to dissolve. Polymers can be synthesised in accordance with the invention at relatively low cost and with high yield. The compositions are thermally, oxidatively and hydrolytically stable in the absence of acid and can be stored ready for use as one-part compositions. Compositions made in accordance with the invention have are produced. Compositions in accordance with the invention have been found to cure tack-free in air and to devlop intense colour during cure. The compositions are potentially useful for use as coatings, sealants, adhesives, potting compositions or photoresists.

The invention will be further described with reference to the accompanying drawings in which.

Figure 3:
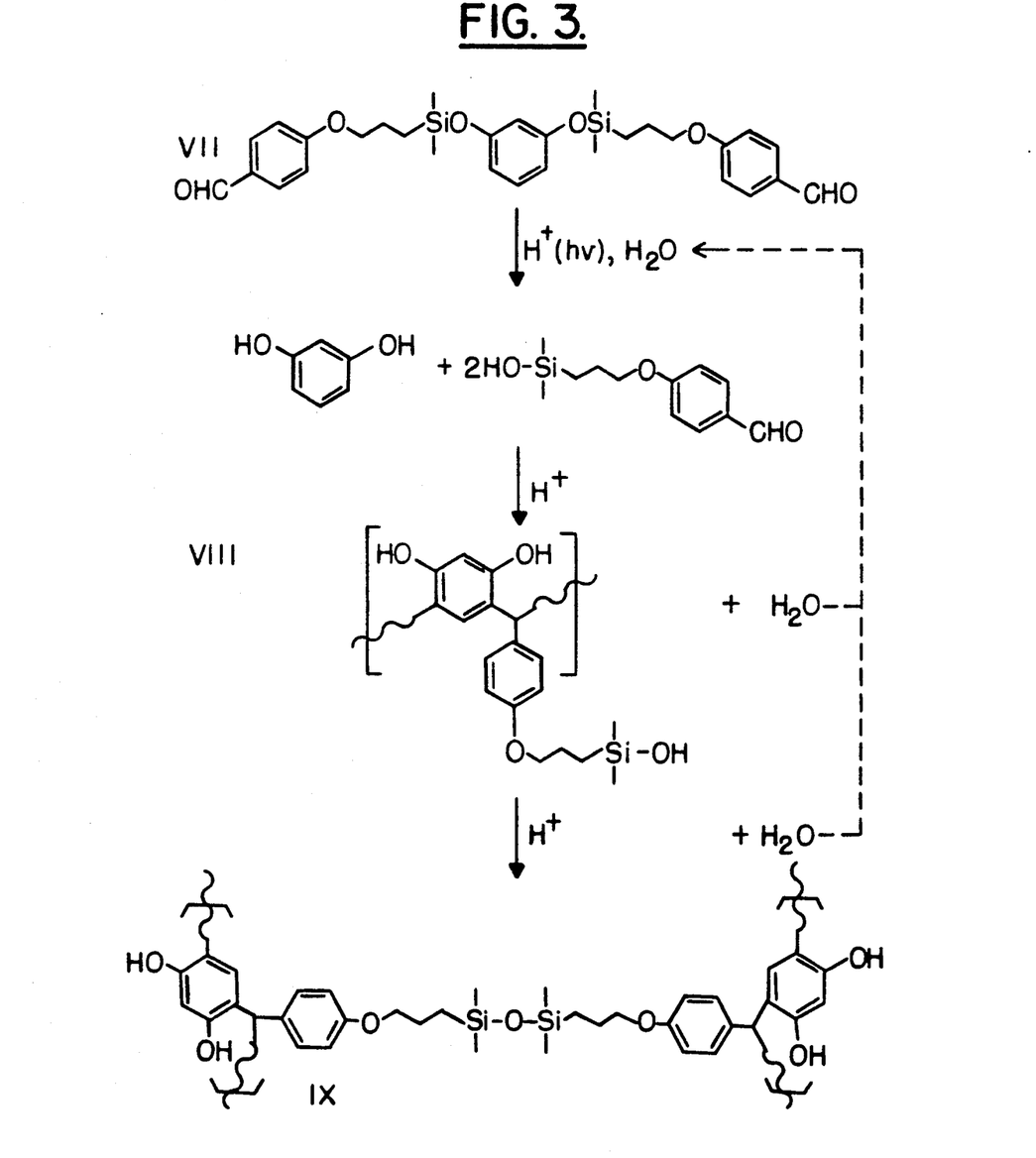
FIG. 3 is a diagram of a proposed reaction mechanism for acid-catalysed polymerization aldehyde functional silyl ethers of resorcinol.

Although the invention is not limited by any theory, it is believed that the polymerisation of the compounds is illustrated by the reaction scheme based on resorcinol silylaldehyde of structure VII shown in FIG. 3 of the drawings. The initial acid hydrolysis reaction produces resorcinol and free silanol-aldehyde. The free phenol and aldehyde then condense to form a partially cross-linked phenolic resin exemplified by structure VIII. The free silanol groups in VIII are believed to further cross link under acid conditions to form a resin of structure IX having siloxane bridges. Water which is required to maintain the initial hydrolysis regenerated at each of the subsequent stages.

EXAMPLE 1

Preparation of the bis-dimethylsilyl ether or resorcinol

Dimethylchlorosilane (118.2 g; 1.25 moles) was added dropwise over 30 minutes to a stirred solution of resorcinol (55 g, 0.5 moles) and 4-dimethylaminopyridine (1.72 g) in pyridine (600 g) at room temperature. After stirring for 16 hours, the mixture was allowed to stand until the precipitate formed during the reaction had settled. The supernatent liquid was decanted and the precipitate washed with diethyl ether (~150 mls). The precipitate was again allowed to settle and the liquid decanted. The process was repeated a further four times and the liquid extracts were combined. The solvent was removed under reduced pressure to yield a yellow oil (103 g) which was fractionated under reduced pressure to give the bis-dimethylsilyl ether of resorcinol at 95–100° C. and 0.8 mbar (81 g, 72%). The structure of the product was confirmed spectroscopically to be as follows:

$^1$H nmr, 60 MHz (CDCl$_3$); 2.8–3.6, multiplet, 4H, aromatic protons, 5.1, septet, 2H, Si-H protons, 9.7 doublet, 12H, Si-CH$_3$ protons.

IR( NaCl, film); 2120 cm$^{-1}$, Si-H stretching vibration.

EXAMPLE 2

Hydrosilation reaction of 4-allyloxybenzaldehyde with the bis-dimethysilyl ether of resorcinol Resorcinol-bis-dimethylsilylether (Example 1) (90.4 g, 0.04 moles) was added gradually over 10 minutes to a stirred solution of 4-allyloxybenzaldehyde (12.96 g, 0.08 moles) chloroplatinic acid (0.15 g of 4 % solution in n-butylacetate) in toluene (22 g) at 65° C. After stirring for an additional 10 minutes, the solvent was removed under reduced pressure to give an oil (22 g). Gel permeation showed the product to consist of mainly one component (>90%), higher in molecule weight than the starting aldehyde. An infra-red spectrum of the product showed absorbance peaks at 1695 cm$^{-1}$ indicating an aromatic carboxyl group; 1420 cm$^{-1}$ and 1255 cm$^{-1}$ indicating Si-CH$_3$ groups and at 85 cm$^{-1}$ due to the Si-C stretching vibration. The product did not show an absorbance at 2120 cm$^{-1}$ indicating complete consumption of the starting silyl ether. The results are consistent with the structure VII:

which is referred to as resorcinol silylaldehyde-1 (RSA-1). Addition of one drop of methanesulfonic acid to the product resulted in the immediate formation of dark red insoluble solid polymer.

EXAMPLE 3

Hydrosilation reaction of 6-heptenal with bis-dimethylsilyl ether of resorcinol

The reaction described in Example 2 was repeated using 6-heptenal in place of the aromatic aldehyde. After work up, a dark coloured oil (22.3 g) was obtained which was found to consist mainly of the bis-silylaldehyde functionalized ether of resorcinol having the structure X:

The structure was confirmed by n.m.r. and I.R. spectroscopy. The product was purified by filtering a charcoal tetrahydrofuran (100 mls) mixture through a "Celite" filter bed and removing the solvent from the filtrate. This yielded 21.9 g of a highly coloured viscous oil which is referred to as RSA-2. Addition of a small quantity of methanesulfonic acid to an aliquiot of the oil resulted in the immediate formation of a deep red coloured crosslinked polymer.

EXAMPLE 4

Photocatalytic polymerization of a surface coating based on RSA-1

A composition was prepared by blending together 5.0 g RSA-1 and 0.2 g of GE1014 (a commercially available photocationic sulfonium salt catalyst from General Electric Corporation). A thin film of the composition (75 μm) was prepared on a microscope glass slide and irradiated for 90 seconds by exposure to a medium pressure mercury arc lamp operating at 80 W/cm. The coated sample was located 20 cms. directly below the light source. During irradiation, the liquid coating had converted to a dry solid red coloured film which was found to be insoluble in acetone. The coating was tack-free.

EXAMPLE 5

Photocured Adhesive based on RSA-1

One drop of the photosensitive composition described in Example 4 was placed between the ends of two microscope glass slides (1 × 3 inches; 2.5 × 7.5 cm.) such that an approximate ½ inch (1.25 cm.) overlap adhesive joint was formed. The assembled joint was exposed to ultraviolet light (UV) under the conditions described in Example 4 for 120 seconds. After this period, attempts to separate the substrates resulted in breakage of the glass which indicates that RSA-1 has useful adhesive properties.

EXAMPLE 6

Adhesion strength of an RSA-1 base composition

Cylindrical steel pins, 1.5 inches (3.8 cm.) in height and 0.25 inches (0.63 cm.) in diameter were grit blasted on one of the flat ends, solvent cleaned and treated with an adhesion primer consisting of a solution of 1% glycidoxypropyl trimethoxysilane and 5% water in methanol. After the solvent of the primer was evaporated, one drop of the adhesive formulation of Example 4 was placed on the treated surface of the pin and a piece of glass plate 6 mm in thickness and approximately 1.5 $cm^2$ was placed on top of the adhesive drop. The assembly was located under the UV lamp, as described in Example 4 and irradiated for three minutes. The bonded assemblies were allowed to stand at RT for 16 hours and the tensile breaking strengths were measured in a dynamic tensile testing apparatus at a constant strain rate of 2 mm/min.

The breaking strengths observed for three samples were as follows:

6.6 MPa
6.6 MPa
4.7 MPa

An unirradiated specimen was found to have no measurable strength.

EXAMPLE 7

Photocatalytic polymerization RSA-1

A photosensitive composition was prepared by blending together 1.0 grams of RSA-2 (prepared as described in Example 3) and 0.02 g cationic photocatalyst GE1014. A thin film of the composition was prepared as described in Example 4. After 30 seconds exposure, the liquid film had cured to a solid dry coating.

EXAMPLE 8

Photocured surface coating of RSA-2 resistant to solvents

A photosensitive composition was prepared by blending together 0.08 g of photocatalyst GE1014 and 2.0 g of RSA-2 (Example 3). A thin film of the composition (75 μm) was prepared and exposed to UV radiation as described in Example 4. After 5 seconds exposure, the coating was tack free. After 60 seconds exposure, a hard glossy coating was obtained which showed excellent adhesion to glass. The coating was resistant to acetone and there was no observable deterioration of adhesion following immersion of the coated substrate in a bath of acetone.

EXAMPLE 9

Photocuring of RSA-2 in thick films

A photosensitive composition was prepared by blending together 5 grams RSA-2 and 0.15 grams of photocatalyst GE1014. An open topped cylindrical plastic mould 8 mm in diameter and 2 mm in depth, with an adjustable base was filled to the top with an accurately weighed quantity of the liquid composition. The filled mould was located 1 cm directly below the tip of a one meter long fluid filled light guide of a Lumatec Superlite-UV 201 high pressure mercury lamp source (supplied by Lumatec GmbH W. Germany) and exposed to the UV radiation for a precise period of time using a timer controlled shutter mechanism. After irradiation the cured or semi-cured slug of material was ejected from the mould by an appropriate adjustment of the mould base, transferred to a small test-tube containing approximately 2 mls. of acetone, sealed and shaken for 30 seconds in a mechanical shaker. The washed polymer slug was dried to constant weight and % gel fraction determined gravimetrically. The results obtained for different exposures were as follows:

| Exposure Time (Mins) | Gel Fraction (Wt %) |
|---|---|
| 0.5 | 32 |
| 1.0 | 36 |
| 2.0 | 40 |
| 3.0 | 54 |
| 5.0 | 51 |
| 10.0 | 53 |

Figure 1:
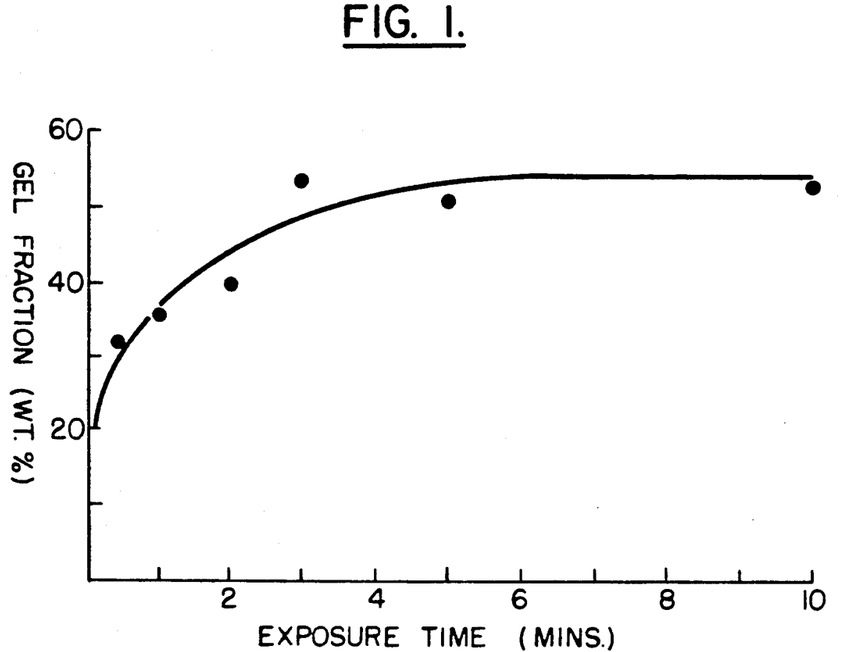
FIG. 1 is a graph of Gel Fraction (weight %) against Exposure Time (minutes) for the composition of Example 9 below.

These data (presented graphically in FIG. 1) show a limiting gel fraction corresponding to approximately 55% or 1.1 mm in depth. This particular composition is therefore suitable for coating, potting and sealing applications requiring cured films up to approximately 1 mm in thickness.

EXAMPLE 10

Post curing Photopolymerized RCA-2

Dark, room temperature, post irradiation curing was observed for the RCS-2/GE1014 composition described in Example 6. The extent of post-curing was determined by measuring the gel fraction for the composition after a dark storage period following initial irradiation. The results obtained were as follows:

| UV Exposure (Mins) | Post Cure Storage (Hrs) | Gel Fraction |
|---|---|---|
| 2 | 0 | 40 |
| 2 | 18 | 53 |
| 2 | 48 | 52 |
| 2 | 115 | 54 |
| 3 | 0 | 54 |
| 3 | 18 | 66 |
| 3 | 48 | 58 |
| 3 | 115 | 62 |

Figure 2:
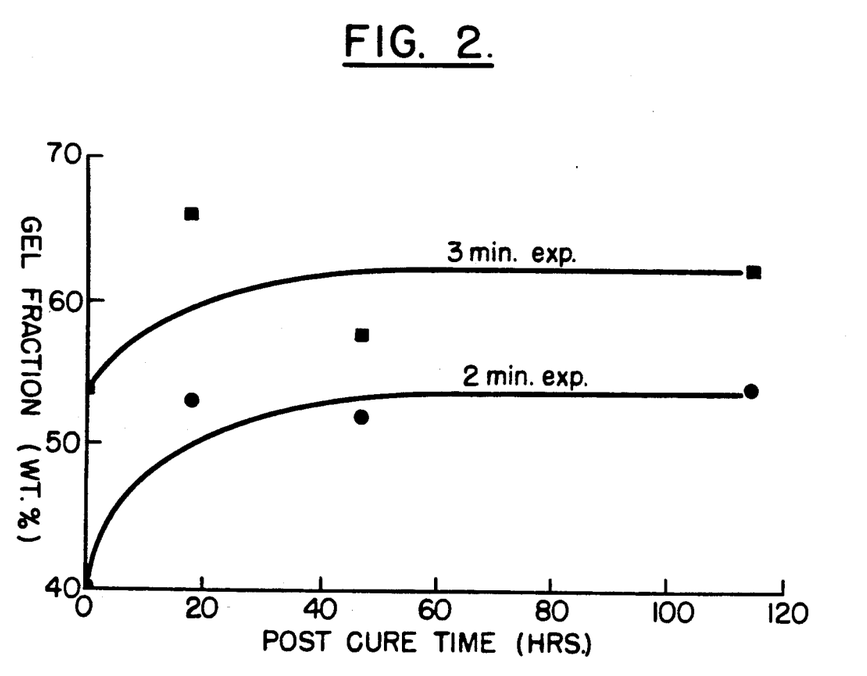
FIG. 2 is a graph of Gel Fraction (weight %) against Post Cure Storage Time (hours) for the composition of Example 10 below.

By plotting the post-cure time against the gel-fraction (shown in FIG. 2) the ultimate increase in gel fraction was found to be 34% for an initial 2 minute exposure and 15% for an initial 3 minute exposure period.

EXAMPLE 11

Bonding Opaque substrates following photoactivation of RSA-1 Composition

The post curing phenomenon described in Example 10 may be used to particular advantage in the bonding of non-UV transmitting substrates following photoactivation of the adhesive layer. To demonstrate this utility, the composition of Example 4 was coated onto the ends of untreated but solvent cleaned mild steel lap shear panels 1×4 inch (2.5×10 cm.). The coated panels were exposed to UV radiation for sufficient time to activate the adhesive composition. Pairs of irradiated panels were then assembled to give ½ inch (1.25 cm.) overlaps, clamped and left for 16 hours for adhesive strength to develop. During irradiation some polymerization was observed. The tensile shear adhesive strength was determined in a tensile tester operating at a constant strain rate 2 mm/minute. The results obtained were as follows:

| Exposure Time (Seconds) | Tensile Shear Breaking Strength (MPa) |
|---|---|
| 0 | 0 |
| 10 | 0.4 |
| 20 | 1.5 |
| 30 | 1.2 |
| 60 | 1.4 |

These data suggest an optimum irradiation period of approximately 20 seconds.

EXAMPLE 12

Heat curable compositions based on RSA-1 and RSA-2

The silylaldehyde ethers of resorcinol RSA-1 and RSA-2 may also be heat cured in the presence of a thermal latent acid catalyst. Such catalyst are known to produce acid when heated to elevated temperatures. The catalyst employed in this example was 2-hydroxycyclohexyl p-toluene sulfonate (HCT). This material was synthesised according to the procedure of M.S. Chatt and D.R. Bauer, *Ind. Eng. Chem. Prod. Res. Dev.*, 22, 440, (1983). It is known to produce p-toluenesulfonic acid and other cationic species when heated to temperatures above 60° C. but shows no significant decomposition below this temperature. The following heat sensitive compositions were prepared by blending the ingredients together:

|  | A | B |
|---|---|---|
| RSA-1 | 3.0 g |  |
| RSA-2 |  | 3.0 g |
| HCT (Heat Catalyst) | 0.06 g | 0.06 g |

0.05 g samples of each formulation A and B were placed in small glass test tubes and placed in an oven at 130° C. side by side with uncatalysed control samples of RSA-1 and RSA-2. After 15 minutes composition B was found to have cured to a hard solvent insoluble solid polymer. After 45 minutes formulation A was similarly cured. After two hours heating both of the control samples were still liquids and showed no change in their original properties.

We claim:

1. Compounds of the formula III:

wherein
R$^1$ and R$^2$ which may be the same or different are selected from H, —R$^3$—X, aliphatic hydrocarbyl having 1-6 carbon atoms or aryl, or substituted derivatives thereof, provided that not more than one of $R^1$ and $R^2$ is H;

$R^3$ is a divalent $C_1$-$C_{30}$ aliphatic and/or hydrocarbyl group which may optionally be substituted, or interrupted, by a hetero atom;

$R^4$ and $R^5$ which may be the same or different are H, or an ortho para directing activating group for aromatic electrophilic substitution, other than an amine;

and X is a reactive functional group capable of undergoing an acid-catalysed electrophilic aromatic substitution reaction with a phenol.

2. Compounds according to claim 1 wherein X is selected form

(a) aldehyde groups (b) cyclic unsaturated acetal groups of the structure or where $R^-$ = H or $CH_3$ (c) benzylic alcohol groups having the structure IV (i), (ii) or (iii):

or which may be further ring substituted with —$CH_3$ groups.

(d) tertiary aliphatic alcohol groups of the structure

(e) allylic ether groups of the structure $R_7$—CH=CH—$CH_2$—O—

(f) propenylbenzene derivatives of the structure V

(g) allylic alcohol groups of the structure HO—$CH_2$—CH=CH—

(h) alkenes of the structure where $R^-$ is as defined above.

3. Compounds according to claim 1 wherein $R^4$ and $R^5$ are selected from $C_1$-$C_{20}$ alkenyl, $C_1$-$C_{20}$ alkoxy, phenoxy, and —NH-C(O)$R^6$ (wherein $R^6$=$C_1$-$C_{16}$ alkyl or phenyl).

4. Compounds according to claim 1 which are of the formula VI:

wherein $R^1$ and $R^2$ are as defined in claim 1, Ph is phenyl, m=0 or 1, and n=1-10.

5. Compounds according to claim 1 wherein $R^1$ and $R^2$ are $C_1$-$C_4$ alkyl.

6. Compounds according to claim 4 which is of the formula VII:

or X